United States Patent [19]

Hirdes

[11] 4,173,236
[45] Nov. 6, 1979

[54] APPARATUS FOR FILLING MAGAZINE OF DENTAL APPLIANCE

[76] Inventor: Rüdiger Hirdes, Tippelsberger Str. 42, 4630 Bochum, Fed. Rep. of Germany

[21] Appl. No.: 882,565

[22] Filed: Mar. 2, 1978

Related U.S. Application Data

[63] Continuation of Ser. No. 750,188, Dec. 13, 1976, abandoned.

[30] Foreign Application Priority Data

Dec. 16, 1975 [DE] Fed. Rep. of Germany ....... 2556574

[51] Int. Cl.² .................................................. B65B 3/12
[52] U.S. Cl. .................................... 141/249; 141/327; 141/378; 248/316 B; 425/406; 433/89
[58] Field of Search .................. 32/60; 53/124 TS; 141/81, 249, 258, 369, 372, 378, 327, 183–191; 164/312; 222/252, 255; 425/79, 256, 376 R, 406; 248/311.1 R, 313, 316 B

[56] References Cited

U.S. PATENT DOCUMENTS

| | | | |
|---|---|---|---|
| 878,761 | 2/1908 | Allen | 141/249 |
| 3,593,761 | 7/1971 | Lorenz | 141/190 X |

Primary Examiner—Frederick R. Schmidt
Attorney, Agent, or Firm—Michael J. Striker

[57] ABSTRACT

An apparatus for charging a plastic mass such as dental amalgam through an opening of and into the hollow interior of a capsule such as a magazine for a tooth-filling appliance has a support formed with an elongated passage defining a longitudinal axis and having an outlet end, with a seat at the outlet end snugly interfittable with the capsule over the opening thereof, and with a storage chamber adapted to hold the mass and extending transversely from the passage. A piston is reciprocal axially within the passage between a retracted position to the opposite side of the chamber as the outlet end and in an advanced position as least substantially past the chamber toward the outlet end. This piston is axially displaceable in the passage between these positions for displacing a charge of the mass from the chamber axially along the passage and out of the outlet end into the capsule through the opening thereof. Means is provided for holding the capsule tightly in place over the end of the passage and a plug fitting into the chamber serves to urge the mass into the passage from which the chamber opens.

10 Claims, 4 Drawing Figures

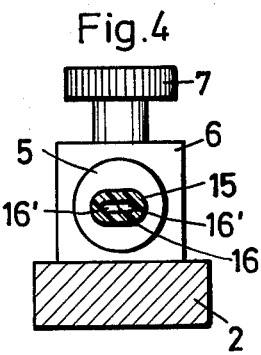
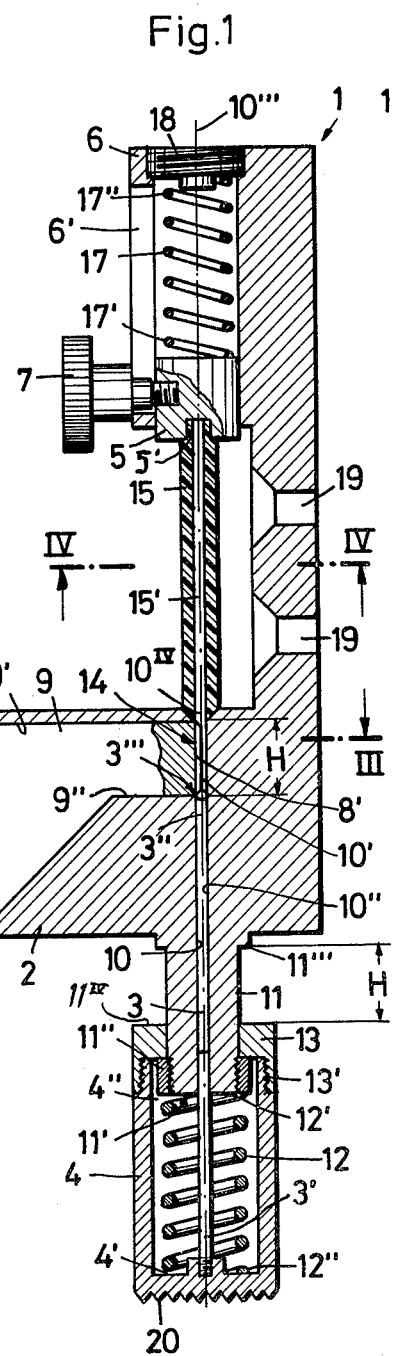
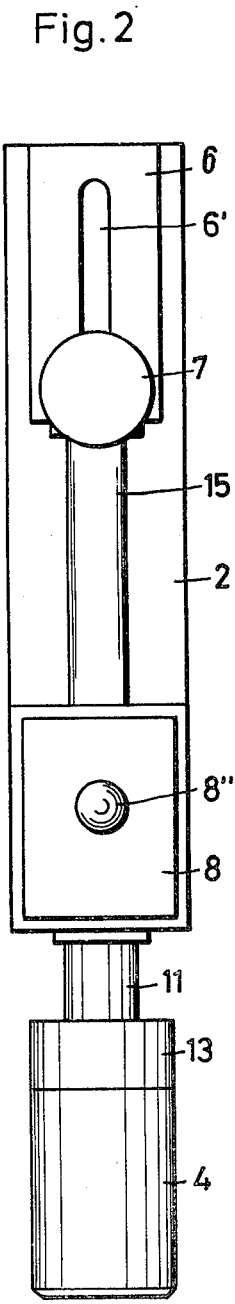
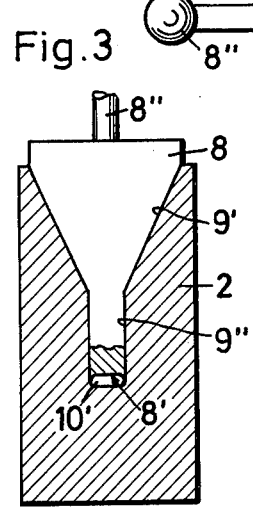

APPARATUS FOR FILLING MAGAZINE OF DENTAL APPLIANCE

This is a continuation of application Ser. No. 750,188, filed Dec. 13, 1976, now abandoned.

CROSS-REFERENCE TO RELATED APPLICATIONS

This application is related to my copending application Ser. No. 535,312 (now U.S. Pat. No. 3,990,152) and to my application Ser. No. 677,886 filed Apr. 19, 1976 (now U.S. Pat. No. 4,092,776), as a division of application Ser. No. 535,312 now U.S. Pat. No. 3,990,152, the disclosures and references of both of these applications being herewith incorporated by reference.

BACKGROUND OF THE INVENTION

The present invention relates to an apparatus for charging a plastic mass into the hollow interior of a capsule or magazine. More particularly this invention concerns an apparatus for injecting dental amalgam into a filling instrument as described in my above-cited copending applications.

My above-cited patent applications, which correspond to German published specification No. 2,364,547, describe a dental appliance for introducing filler material into a tooth cavity. This appliance comprises an elongated support carrying at one end a discharge nipple having elongated interior channels formed with an outlet opening transversely of the support, an inlet opening longitudinally of the support, and a lateral opening intermediate the inlet and the outlet and itself opening longitudinally of the support. Means is provided in the support forming a passage having an open end directed generally longitudinally of the support toward the nipple and in line with the lateral opening. A replaceable capsule or magazine is engageable between the open end and the lateral opening and has a throughgoing chamber adapted to hole a body or mass of the filler material and open to the open end and to the lateral opening. A first expelling element is reciprocal through the passage and the chamber. A first piston is carried on this first element. A first cylinder is provided in the housing surrounding the first piston and subdivided thereby into a front compartment and a rear compartment. First a valve means is effective in a first position for feeding air under pressure into the rear compartment and thereby advancing the first element through the chamber to push material therein into the channel through the lateral opening and effective in a second position to withdraw the element from the chamber into the passage. A second expelling element is formed as a flexible wire having a tip reciprocal in the passage past the lateral opening. A second piston is carried on this second element. A second cylinder is provided in the housing surrounding the second piston and subdivided thereby into a front compartment and a rear compartment. Second valve means is effective in one position for supplying air under pressure to the rear compartment of the second cylinder to push the tip in the channel past the lateral opening toward the outlet and effective in another position for withdrawing the tip away from the outlet past the lateral opening.

Such a device serves to inject the amalgam mixture into a tooth cavity. Further such devices are described in German published specification No. 1,491,002, British Pat. No. 934,235 and U.S. Pat. Nos. 3,623,224 and 3,638,314. U.S. Pat. No. 3,751,807 as well as my above-cited copending applications describe such a system wherein the entire filling apparatus need not be taken out of use during filling, as such devices have a removable capsule or magazine which can be separated from the apparatus and then filled. This system allows the dentists technician to fill extra magazines or capsules while the dentist himself or herself is filling the tooth.

It is necessary to prepare an amalgam mixture, normally comprising by weight 65% silver, 25% tin, 6% copper, 2% zinc, 3% mercury and traces of gold and platinum. Such a standard amalgam mixture remains plastic for between 5.0 and 10.0 minutes after it is mixed up, and hardens completely after approximately 2.0 hours. It is therefore necessary to combine the ingredients, mix them, load the filling device, inject the mixture into the cavity with the filling device, and shape and tamp the filling thus formed within 5 or 10 minutes. It is possible to speed the mixing time by using a vibrating amalgamator that insures almost instantaneous mixing of the above-mentioned ingredients. The bottleneck in the operation typically lies in transferring the ready-to-use mixture to the filling appliance. No practical solution has yet been presented to speed this operation.

SUMMARY OF THE INVENTION

It is therefore an object of the present invention to provide an improved system for filling a plastic mass into a capsule or the like.

Another object is to provide an improved apparatus for charging a load of amalgam or resin into the interior of a magazine or capsule of a dental filling appliance.

Yet another object is to provide such an apparatus which can operate extremely rapidly so as to maximize the time left to the dentist for tamping and shaping a filling.

These objects are attained according to the present invention in an apparatus for charging a plastic mass through an opening of and into the hollow interior of a capsule. This apparatus has a support formed with an elongated passage defining a longitudinal axis and having an outlet end, with a seat at the outlet end snugly interfittable with the capsule over the opening thereof, and with a storage chamber adapted to hold the mass and extending transversely from the passage. A piston is axially reciprocal in the passage between a retracted position to the opposite side of the chamber as the outlet end of the passage and in advanced position at least substantially past the chamber toward the outlet end of the passage. Means is provided for displacing this piston axially in the passage between these positions for displacing a charge of the plastic mass from the chamber axially along the passage and out of the outlet end of the passage into the capsule through the opening of the capsule which is juxtaposed with the seat of the support.

In accordance with another feature of this invention the capsule is generally tubular and the interior thereof is of regular cross-sectional area and shape. Similarly the passage is of regular cross-sectional area and shape, but slightly smaller than the interior of the capsule. Thus the piston will push into the interior of the capsule a charge or plug of plastic mass which is slightly smaller in cross-sectional area than the interior of the capsule, insuring a realtively easy filling of this capsule.

With the system according to the present invention it is therefore possible to load the mixed amalgam directly from the amalgamator into the chamber of the device, after having fitted a magazine or capsule to it. Then the piston is reciprocated one or more times to fill the capsule, whereupon this filled capsule or magazine can be loaded into the filling apparatus. As the densist is occupied then injecting the amalgam into the cavity, the dental assistant can be filling other magazines so that the entire filling operation can easily be executed in the short time during which the amalgam remains plastic.

According to yet another feature of this invention the chamber has a portion adjacent the passage and of regular cross-sectional area, centered on an axis perpendicular to the axis of the passage. In addition this chamber has an outer portion of outwardly flared or frustoconical shape so as to simplify loading of the amalgam mass into the chamber. A plug shaped complementarily to the two-portion chamber can be fitted into this chamber after a mass has been loaded in in order to press it toward the passage. The end of this plug turned toward the passage is concave and shaped so as to form a continuous extension of the inner wall of the passage when the plug is pressed all the way in. Thus it is possible for all of the amalgam mixture in the filling device for the magazine to the loaded into the magazine, eliminating the necessity of painstakingly cleaning the arrangement afterward. When the device is made with close tolerances and of a material having a very low coefficient of friction, such as polytetrafluoroethylene, it is therefore possible to completely empty the arrangement.

According to yet another feature of this invention the piston is formed as an elongated rod of regular cross-sectional area and shape. Its one end turned toward the outlet end of the passage is concave so as to assure good sealing between the piston and the wall of the passage. Its other end projects outwardly from the support through a cylindrical extension on the support centered on the axis defined by the rod. This outer end of the rod carries a cup open backwardly toward the support, and a spring braced between this cup and the support urges the piston into the retracted position. Stops on the piston rod and on the support define this retracted position with the other end of the piston rod lying outside the chamber. The stroke of the piston, that is that axial distance through which it moves between its opposite end positions, is equal to less than half the overall length of the interior of the magazine. Thus at least two, and preferably three or four, reciprocations of the piston are necessary in order to fill the magazine.

In accordance with another feature of this invention the apparatus is provided on the support with means for holding the magazine in place over the seat at which the passage opens. This means includes a guide extending axially in line with the passage but spaced from the outlet end. A holding block formed with a seat for the opposite side of the magazine is axially slidable along this guide, and a spring is provided for urging it axially toward the passage. In addition means is provided for locking it in any axial position. Thus the block can be slid up in the guide against the spring force, a magazine fitted between the two seats, and the block slid back down or allowed to move down under the spring force until the magazine is snugly held between the two seats. Thereafter the holding means can be tightened, simply by rotating a knob to bear tightly on the guide, in order to fix the magazine in place.

According to yet another feature of this invention both the passage in the support and the interior of the magazine are of a cross-sectional shape having a pair of parallel flat and long sides joined by a pair of opposite and inwardly concave short sides. Such a formation allows a good quantity of amalgam to be charged into the magazine for quickest possible filling of the tooth cavity.

The novel features which are considered as characteristic for the invention are set forth in particular in the appended claims. The invention itself, however, both as to its construction and its method of operation, together with additional objects and advantages thereof, will be best understood from the following description of a specific embodiment when read in connection with the accompanying drawing.

BRIEF DESCRIPTION OF THE DRAWING

FIG. 1 is an axial section through the apparatus according to this invention;

FIG. 2 is a top view of the apparatus shown in FIG. 1; and

FIGS. 3 and 4 are sections taken along lines III—III and IV—IV of FIG. 1.

DESCRIPTION OF THE PREFERRED EMBODIMENT

As shown in FIGS. 1 and 2 the apparatus 1 according to this invention generally comprises a block-like support 2 formed with an axis-defining elongated passage 10 in which is axially reciprocal a piston or rod 3. A push-type slide 4 is connected to one end of the piston 3, and a magazine 15 can be held on the device by means of a holding block 5 axially reciprocal in a slide 6 and lockable thereon by means of a screw 7. The support 1 is further formed with a funnel-shaped chamber 9 in which is fittable a complementarily shaped plug 8.

In accordance with this invention the piston or rod 3, the passage 10 and the passage 15' through the magazine tube 15, which corresponds to element 3 of my above-cited copending applications, are all of the same cross-sectional shape. As best shown in FIG. 4 this cross-sectional shape is formed as an elongated ellipse, having a pair of relatively long but straight and planar sides 16 joined by a pair of relatively short and part-cylindrical sides 16'. The piston 3 fits as closely as possible within the chamber 10 which is of regular cross-sectional shape and area. The passage or interior 15' of the tube 15 is of the exact same cross-sectional shape, but is slightly larger than the passage 10 so that a plug of plastic mass pushed from the passage 10 can slide easily into the interior 15'.

The passage 10 has a section 10' at the chamber 9 and another section 10'' which extends outwardly through a circular-section extension 11 formed on the support 2 and centered on the axis 10''' of the passage 10. The piston 3 has a rear end 3' normally projecting from the extension 11 and a front end 3'' having a concave tip 3''' which lies in the illustrated retracted position of the piston 3 at the edge of the chamber 9, spaced from the outlet end $10^{IV}$ of the passage 10.

The pusher or slider 4 is threaded onto the rear end 3' of the piston 3 and a helical compression spring 12 has one end 12' bearing against the end face 11' of the extension 11 and another end 12'' bearing against the confronting face 4' of the slider 4. Thus the slider 4 defines a chamber 4'' in which is housed this spring 12. A collar or abutment ring 11'' is threaded onto the end of the extension 11 and a collar or abutment ring 13 is threaded at 13' onto the end of the pusher 4 toward the support 2. This pusher 4 further is formed on its face turned away from the support with a ridged surface 20 adapted to be pressed by the hand. The extension 11 has a shoulder 11''' abuttable against the confronting end surface 11$^{IV}$ of the pusher 4, the distance between these two surfaces 11''' and 11$^{IV}$ defining the stroke H of the piston 3.

The chamber 9 has a flared outer portion 9' and a rectangular-section inner portion 9'' opening into the passage 10 and of a regular cross-sectional shape and area. The plug 8 in the chamber 9 is shaped exactly complementarily to the chamber 9 and has an end 8' which is of the exact shape of half of the cross-sectional area of the passage 10', bisected parallel to the long sides 16 and through the center of the part-cylindrical short sides 16'. Thus when pushed all the way into the chamber 9 as illustrated this surface 8' forms a continuation of the wall of the passage 10. In addition the plug 8 is provided with an actuating handle 8''.

The guide 6 is centered on the axis 10''' so that the plug or block can slide along this axis 10'''. The lower face of this block is formed with a seat 5' adapted snugly to interfit with the upper end of the cartridge or capsule 15. The screw 7 extends through an axially extending slot 6' in the guide and can be used both to vertically displace the block 5 and to lock it in place by screwing the inner face of the screw-knob 7 tight against the face of the guide 6. A spring 17 within the guide 6 has a lower end 17' bearing on the upper face of the block 5 and an upper end 17'' bearing on the lower face of a screwed-in plug 18 closing the upper end of the spring chamber formed by the guide 6.

The support 2, which is formed with countersunk holes 19 facilitating its mounting on a surface, is formed along with the plug 8 and the magazine 15 of a heat-resistant material such as polytetrafluoroethylene which has a very low coefficient of friction so that the amalgam will not adhere to it, and so that the assembly can be sterilized. The pin 3, the slide 4, the block 5, the screw 7, as well as the two compression springs 12 and 17 are made of corrosion-resistant steel alloy.

The apparatus according to the present invention is used as follows:

A sufficiently large mass of amalgam is made up to fill all of the cavity or cavities that the dentist is working on at the moment. This mass is then charged into the chamber or funnel 9 after removal therefrom of the plug 8. The mass will never be so large that it will extend beyond the portion 9'' of regular cross-sectional area of this funnel 9. Thereupon the screw 7 is loosened and the block 5 is slid away from the outlet 10$^{IV}$, so that a capsule or magazine 15 can be fitted between the seats 5' and the outlet end 10$^{IV}$. The block 5 is then slid down to hold the magazine 15 tightly in place and the screw 7 tightened to prevent it from moving.

Thereafter the plug 8 is fitted into the funnel 9 and pressed down so as to compress the amalgam mass in the region 14 of the passage 10. This region 14 has an overall height H equal to the stroke of the rod 3.

Thereafter the dentist or operator need merely push on the slider 4 while maintaining pressure on the handle 8'' of the plug 8. Such a pushing will force a plug of the amalgam into the larger-section passage 15' in the magazine 15. After four or five such actuations, during which time pressure is maintained on the plug 8, the magazine 15 is filled.

The screw 7 can then be loosened, the filled magazine 15 taken out and fitted to the cavity-filling appliance as described in my above-cited copending applications. As the dentist uses this appliance to fill the cavities the dental technician can be filling other such magazines so as to allow the dentist rapidly to refill his or her cavity-filling appliance and to work continuously.

Since the rod 3 fits exactly within the bore 10 and since the wall 8' of the plug 8 forms at the region 14 an exact continuation of the wall of the bore 10, it is possible to operate the device until all of the amalgam has been pressed from the outlet end 10$^{IV}$. Thus the device does not become rapidly fouled and can be used a long time between cleanings.

It is noted that if a magazine 15 of different cross-sectional shape or length is used, it is possible readily to modify the shape of the seats 5' and 10$^{IV}$ so as to fit whatever shape is used.

It will be understood that each of the elements described above, or two or more together, may also find a useful application in other types of structures differing from the types described above.

While the invention has been illustrated and described as embodied in a magazine-filling apparatus, it is not intended to be limited to the details shown, since various modifications and structural changes may be made without departing in any way from the spirit of the present invention.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. An apparatus for charging a moldable plastic dental amalgam mass into the hollow interior of a capsule formed as an elongated magazine tube having a pair of opposite ends and an opening at each end, said hollow interior of said capsule with said openings having a uniform cross-sectional shape, said apparatus comprising a support formed with an elongated passage defining a longitudinal axis and having an outlet end, with a first seat on said outlet end, said seat being snugly fittable with one of the ends of the capsule in a ready position thereof generally aligned with said axis, said support having a guiding passage extending substantially axially of said support in line with said outlet end; holding means including a rigid member in said guiding passage and having a second seat being snugly fittable with the other end of the capsule in a ready position thereof generally aligned with said axis, and resilient means in said guiding passage for normally urging said rigid member towards said first seat, said rigid member being slidable in said guiding passage on said support towards and away from said first seat against the biasing force of said resilient means; a clamping element for clamping said rigid member in a desired position in said guiding passage to thereby provide a rigid holder for said capsule; means for supplying a moldable plastic mass into said elongated passage in said support; and piston means displaceable axially in said passage between a retracted position in a direction away from said first seat and an advanced position to thereby displace a charge of the moldable plastic mass contained in said passage axially along thereof and out of said outlet end into said capsule through the one opening thereof wherein said outlet end of said elongated passage in said support has a cross-sectional shape similar to that of the capsule, said support being provided with a storage chamber adapted to hold the moldable plastic mass and extending transversely from and opening into said elongated passage, and wherein said moldable-plastic-mass supplying means includes a plug snugly fitting in said chamber and displaceable therein transversely of said axis towards and away from said elongated passage for urging a quantity of the moldable plastic mass in said chamber towards and into said elongated passage.

2. The apparatus defined in claim 1, wherein said interior and said outlet end are of substantially the same regular cross-sectional area, said elongated passage being of a regular cross-sectional area at most as large as said area of said interior and said outlet end.

3. The apparatus defined in claim 2, wherein said area of said elongated passage is slightly smaller than said area of said interior and outlet end.

4. The apparatus defined in claim 2, wherein each of said areas is shaped with a pair of generally parallel long sides and a pair of oppositely inwardly concave and short curved sides.

5. The apparatus defined in claim 2, wherein said chamber has a portion opening into said elongated passage of regular cross-sectional shape seen in a direction transverse to said axis.

6. The apparatus defined in claim 5, wherein said plug snugly fits in said portion.

7. The apparatus defined in claim 6, wherein said chamber has a portion extending from said portion of regular cross-sectional area and flaring away from said elongated passage, said plug being shaped complementarily to said portions of said chamber.

8. The apparatus defined in claim 6, wherein said plug has an inner end of generally concave shape and displaceable into a position forming a continuation of the interior walls of said passage on full insertion of said plug into said chamber.

9. The apparatus defined in claim 2, wherein said piston has an end portion that projects from said support in said retracted position of said piston.

10. An apparatus as defined in claim 1, wherein said piston means include a piston reciprocal axially in said passage between the retracted position to the opposite side of said chamber as said outlet end and the advanced position at least substantially past said chamber towards said outlet end.

* * * * *